United States Patent [19]
Cros et al.

[11] Patent Number: 5,695,926
[45] Date of Patent: Dec. 9, 1997

[54] SANDWICH HYBRIDIZATION ASSAYS USING VERY SHORT CAPTURE PROBES NONCOVALENTLY BOUND TO A HYDROPHOBIC SUPPORT

[75] Inventors: Philippe Cros, Lyons; Patrice Allibert, Grezieu la Varenne; François Mallet, Villeurbanne; Claude Mabilat, Villeurbanne; Bernard Mandrand, Villeurbanne, all of France

[73] Assignee: Bio Merieux, Marcy-L'Etoile, France

[21] Appl. No.: 255,892

[22] Filed: Jun. 7, 1994

Related U.S. Application Data

[63] Continuation of Ser. No. 834,543, filed as PCT/FR91/00468, Jun. 11, 1991 published as WO91/19812, Dec. 26, 1991, abandoned.

[30] Foreign Application Priority Data

Jun. 11, 1990 [FR] France ................... 90 07249

[51] Int. Cl.$^6$ .................. C12Q 1/70; C12Q 1/68
[52] U.S. Cl. ............................ 435/5; 435/6
[58] Field of Search .............. 435/6, 5; 935/78; 436/94

[56] References Cited

U.S. PATENT DOCUMENTS

| | | | |
|---|---|---|---|
| 4,379,843 | 4/1983 | Cashion | 435/178 |
| 4,486,539 | 12/1984 | Ranki et al. | 436/504 |
| 4,994,373 | 2/1991 | Stavrianopoulus et al. | 435/6 |
| 5,232,829 | 8/1993 | Longiaru et al. | 435/6 |

FOREIGN PATENT DOCUMENTS

| | | |
|---|---|---|
| 0202758 | 11/1986 | European Pat. Off. |
| 0269764 | 6/1988 | European Pat. Off. |
| 0405592 | 1/1991 | European Pat. Off. |
| 0405913 | 1/1991 | European Pat. Off. |
| 0420260 | 4/1991 | European Pat. Off. |
| 8607387 | 12/1986 | WIPO |
| 8801302 | 2/1988 | WIPO |
| 8804301 | 6/1988 | WIPO |
| 9001069 | 2/1990 | WIPO |

OTHER PUBLICATIONS

Saiki et al., *Nature* 324, 163–166(1986).
Syvänen et al., *Nucleic Acids Res.* 14(12), 5037–5048(1986).
Meinkoth et al., *Analyl. Biochem.* 138, 267–284 (1984).
Lacy et al., *J. Immun. Methods* 116, 87–98 (1989).
Inouye et al., *J. Clin. Micro.* 28(6), 1469–1472 (1990).
Polsky–Cynkin et al, "Use of DNA immobilized on plastic and agarose supports to detect DNA by sandwich hybridication", Clinical Chemistry, vol. 31, No. 9, 1985, p. 1439.
Helsingius et al, "Solid–phase immunoassay of digoxin by measuring time–resolved fluorescence", Clinical Chemistry, vol. 32, No. 9, 1986, pp. 1767–1769.
Current Protocols in Molecular Biology, vol. 1 (1993), Wiley & Sons, Inc., pp. 2.9.1–2.9.2.

*Primary Examiner*—Kenneth R. Horlick
*Attorney, Agent, or Firm*—Nixon & Vanderhye, P.C.

[57] ABSTRACT

A procedure for detecting single-stranded nucleotide sequences in a sample is disclosed wherein a passively fixed capture probe is used in concert with a non-radioactively labelled detection probe in a sandwich hybridization technique.

23 Claims, 1 Drawing Sheet

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCACTGCATA ATTCTT                                                    1 6

( 2 ) INFORMATION FOR SEQ ID NO:2:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AAGGTCAACC GGAATTTCAT TTTGGGGCTC TAAATGCAAT ACAATGTCTT GCAATGTTGC    6 0

CTTA                                                                 6 4

( 2 ) INFORMATION FOR SEQ ID NO:3:

( i ) SEQUENCE CHARACTERISTICS:
        ( A ) LENGTH: 23 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GAAGCTGTTA GACATTTTCC TAG                                    23

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACCCCGAGAT TTACGTTATG T                                       21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ACCCCGAGAT TTACGTTATG T                                       21

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GAACAGCCAG AAGGAC                                             16

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AACGCTACTA CTATTAGTAG                                         20

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TACTGTCATG CCATCC 16

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TGCATTTAGA GCC 13

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GCATTTAGAG CC 12

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCATTTAGAG C 11

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CATTTAGAG 9

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CCGGGCGGTG ACGGAGCTGG GGC 23

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TACTGTCATG CCATCC         16

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TTGCATTTAG AGCCC         15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TTGCATTTAG AGCCC         15

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GTTGGCCGCA GTGTTAT         17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CACTCATGGT TATGGCA         17

( 2 ) INFORMATION FOR SEQ ID NO:19:

( i ) SEQUENCE CHARACTERISTICS:
        ( A ) LENGTH: 16 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GGATGGCATG ACAGTA 16

( 2 ) INFORMATION FOR SEQ ID NO:20:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

AGAGAATTAT GCAGTGC 17

( 2 ) INFORMATION FOR SEQ ID NO:21:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

TGCCATAACC ATGAGTG 17

( 2 ) INFORMATION FOR SEQ ID NO:22:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

ATAACACTGC GGCCAAC 17

( 2 ) INFORMATION FOR SEQ ID NO:23:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

ATCAGCAATA ACCAGC 16

( 2 ) INFORMATION FOR SEQ ID NO:24:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

CCCCGAAGAA CGTTTTC                                                                 17

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TACACTGCTG GACAACATGC                                                              20

( 2 ) INFORMATION FOR SEQ ID NO:26:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTGCGCAGAT GGGACACAC                                                               19

( 2 ) INFORMATION FOR SEQ ID NO:27:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CAGTGTACAG AAACA                                                                   15

( 2 ) INFORMATION FOR SEQ ID NO:28:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GAGTGCACAG ACGGA                                                                   15

( 2 ) INFORMATION FOR SEQ ID NO:29:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GACCCTGTAG GGTTACATT                                                               19

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TACACTGCTG GACAACATGC                                 20

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GTGCGCAGAT GGGACACAC                                  19

( 2 ) INFORMATION FOR SEQ ID NO:32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GAGTGCACAG ACGGA                                       15

( 2 ) INFORMATION FOR SEQ ID NO:33:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CAACTACAAG ACCTTTTGC                                  19

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

TACACTGCTG GACAACATGC                                 20

( 2 ) INFORMATION FOR SEQ ID NO:35:

( i ) SEQUENCE CHARACTERISTICS:
        ( A ) LENGTH: 19 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:35:

GTGCGCAGAT GGGACACAC 19

( 2 ) INFORMATION FOR SEQ ID NO:36:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:36:

AGACAGCTCA GAAGATGAGG 20

( 2 ) INFORMATION FOR SEQ ID NO:37:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:37:

CAGCAACGTT CGACTGGTTG 20

( 2 ) INFORMATION FOR SEQ ID NO:38:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:38:

CCCAGCTGTA ATCATGCATG GAGA 24

( 2 ) INFORMATION FOR SEQ ID NO:39:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:39:

GTGTGCCCAT TAACAGGTCT TCCA 24

( 2 ) INFORMATION FOR SEQ ID NO:40:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:40:

TATATGTTAG ATTTGCAACC 20

( 2 ) INFORMATION FOR SEQ ID NO:41:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GACAACTGAT CTCTAC 16

( 2 ) INFORMATION FOR SEQ ID NO:42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CCGGACAGAG CCCATTAC 18

( 2 ) INFORMATION FOR SEQ ID NO:43:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CTCTACGCTT CGGTTGTGC 19

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

CGACAGGAAC GACTCCAACG 20

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GCTGGTAAAT GTTGATGATT AACT 24

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TCAGAGGAAG AAAACGATGA        20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

ATGTCACGAG CAATTAAGCG        20

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

GTATTGCATT TAGAGCCCCA        20

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

TAAGGCAACA TTGCAAGACA        20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50 :

CACCATAGTA ACCCATACGC        20

( 2 ) INFORMATION FOR SEQ ID NO:51:

( i ) SEQUENCE CHARACTERISTICS:
        ( A ) LENGTH: 21 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:51:

GCCGCTTTGA GTTCTGCTTC C         21

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

GGCGGCCTGA TGCCGAGTAC         20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CTTGCAAGCT CTGCCTGTGG         20

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

AATCCTGGCT GAACCAAGCC T         21

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

AAGGTTTCGG CGGAGATCCT         20

(2) INFORMATION FOR SEQ ID NO:56:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:56:

GGACATCAAG CAGCCATGC  19

( 2 ) INFORMATION FOR SEQ ID NO:57:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

CTAGTAGTTC CTGCTATGTC  20

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

AATGTTAAAA GAGAC  15

( 2 ) INFORMATION FOR SEQ ID NO:59:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

GAAGCTGCAG AATGGGA  17

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

CTTGTTGTCC CTGCTATGTC  20

( 2 ) INFORMATION FOR SEQ ID NO:61:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

CTTACCAGCG GGGCAGC  17

( 2 ) INFORMATION FOR SEQ ID NO:62:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CAGGAAGCAC TATGGGCGC                                                            19

( 2 ) INFORMATION FOR SEQ ID NO:63:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GCTGCTTGAT GCCCCAGAC                                                          19

( 2 ) INFORMATION FOR SEQ ID NO:64:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

TGTCTGGTAT AGTGCA                                                              16

( 2 ) INFORMATION FOR SEQ ID NO:65:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

AACAATTTGC TGAGGGCTAT                                                    20

( 2 ) INFORMATION FOR SEQ ID NO:66:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CAGGCAGTTC TGCAATGGG                                                      19

( 2 ) INFORMATION FOR SEQ ID NO:67:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:67:

GGTTTTTCGT TCCCCAGACG 20

( 2 ) INFORMATION FOR SEQ ID NO:68:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:68:

GCAACAGCAA CAGCTGTTGG A 21

( 2 ) INFORMATION FOR SEQ ID NO:69:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:69:

GGTCAAGAGA CAACAAGAA 19

( 2 ) INFORMATION FOR SEQ ID NO:70:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:70:

ATTAGCAGGA AGATGGCCAG 20

( 2 ) INFORMATION FOR SEQ ID NO:71:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:71:

CTGCCATTTG TACTGCTGGT C 21

( 2 ) INFORMATION FOR SEQ ID NO:72:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:72:

GACAATGGCA GCAATTTCAC C        21

( 2 ) INFORMATION FOR SEQ ID NO:73:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

GCCTGTTGGT GGGC        14

( 2 ) INFORMATION FOR SEQ ID NO:74:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

CAATACGCTC GAACGACGT        19

( 2 ) INFORMATION FOR SEQ ID NO:75:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

CACGGGTTGG GGTTTCTAC        19

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

TGGCTTCTGT CAACGCTGTT        20

( 2 ) INFORMATION FOR SEQ ID NO:77:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

ATGCGATCTA TATCACGCTG        20

( 2 ) INFORMATION FOR SEQ ID NO:78:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

GATCGCGGTG TCAGTTCTTT     20

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

TTCCATGGGT TTCTCACAGA     20

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

GACTCAGAAT AATCCAGCCT     20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

TGTTTACGCA GTCTGCCTAG     20

( 2 ) INFORMATION FOR SEQ ID NO:82:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

GTCCAATGCC AGGTGGATGA     20

( 2 ) INFORMATION FOR SEQ ID NO:83:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:83:

CACATATTGA CCAAATCAGG                                                     20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

GTATCATGCC TCTTTGCACC                                                     20

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

TTTCTGGGTT AAGGCAATAG C                                                   21

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

TGTTATGATG GTGAAACCTG                                                     20

(2) INFORMATION FOR SEQ ID NO:87:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

CTGTAGAGGT TAATATCCGC AAA                                                 23

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:88:

CAGTGCCATG AGAGACCAAT                                                                                                20

( 2 ) INFORMATION FOR SEQ ID NO:89:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

CGACGCAGCC ATGGTCGATG C                                                                                              21

( 2 ) INFORMATION FOR SEQ ID NO:90:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

TTCCTCTGTG TATTTGCCAT                                                                                                20

( 2 ) INFORMATION FOR SEQ ID NO:91:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

TCATCGTTTT CTTCCTCTGA GTCGCTTAAT TGCTCGTGAC ATAGAAGGTC AACCGGAATT                                                     60

TCATTTTGGG GCTCTAAATG CAATACAATG TCTTGCAATG TTGCCTTA                                                                  108

( 2 ) INFORMATION FOR SEQ ID NO:92:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:92:

AAGGTCAACC GGAATTTCAT TTGGGGCTA TAAATGCAAT ACAATGTCTT GCAATGTTGC                                                      60

CTTA                                                                                                                 64

( 2 ) INFORMATION FOR SEQ ID NO:93:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:93:

ACCCCGAGAT TTAGGTTATG T                                                                           21

( 2 ) INFORMATION FOR SEQ ID NO:94:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

AAGGTCAACC GGAATTTCAT TTGGGGCTC TATATGCAAT ACAATGTCTT GCAATGTTGC        60

CTTA                                                                   64

( 2 ) INFORMATION FOR SEQ ID NO:95:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

CATTGGTCTT AAAGGTACCT G                                                21

( 2 ) INFORMATION FOR SEQ ID NO:96:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

AAGATGGGTG GCAANTGGTC                                                  20

( 2 ) INFORMATION FOR SEQ ID NO:97:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

GAGGAGGTNG GTTTTCCAGT CA                                               22

( 2 ) INFORMATION FOR SEQ ID NO:98:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

TGGAACAAGC CCCANGAGAC C                                                21

( 2 ) INFORMATION FOR SEQ ID NO:99:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

TGCTATGTNG ACACCCAATT CTG    23

( 2 ) INFORMATION FOR SEQ ID NO:100:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:100:

TATGAAACTT ATGGGGATAC    20

( 2 ) INFORMATION FOR SEQ ID NO:101:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:101:

AAGGTCAACC GGAATTTCAT TTTGGGGCTC AAAATGCAAT ACAATGTCTT GCAATGTTGC    60

CTTA    64

( 2 ) INFORMATION FOR SEQ ID NO:102:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:102:

TGAACAAGTA GATAAATTAG    20

( 2 ) INFORMATION FOR SEQ ID NO:103:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

GGAATCAGNA AAGTACTATT    20

( 2 ) INFORMATION FOR SEQ ID NO:104:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:104:

CCGGGCGGTG ACTGAGCTGG GGC    23

( 2 ) INFORMATION FOR SEQ ID NO:105:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:105:

ACATGAGGAC AGGCGAAGGC    20

( 2 ) INFORMATION FOR SEQ ID NO:106:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:106:

TGACCTGTTG CTGTGGA    17

( 2 ) INFORMATION FOR SEQ ID NO:107:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:107:

TTGCATTTAG AGCCC    15

( 2 ) INFORMATION FOR SEQ ID NO:108:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:108:

GACCATCAAG CAGCCATGC    19

( 2 ) INFORMATION FOR SEQ ID NO:109:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:109:

GAAGCTGCAG AATGGGA        17

( 2 ) INFORMATION FOR SEQ ID NO:110:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:110:

GGATGGCCTN CTNTAAGGGA AAGAATG        27

( 2 ) INFORMATION FOR SEQ ID NO:111:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:111:

CAGCAACGTC CGACTGGTTG        20

( 2 ) INFORMATION FOR SEQ ID NO:112:

( i ) SEQUENCE CHARACTERISTICS:
  ( A ) LENGTH: 64 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:112:

AAGGTCAACC GGAATTTCAT TTTGGGGCTC TGAATGCAAT ACAATGTCTT GCAATGTTGC        60

CTTA        64

( 2 ) INFORMATION FOR SEQ ID NO:113:

( i ) SEQUENCE CHARACTERISTICS:
  ( A ) LENGTH: 63 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:113:

AAGGTCAACC GGAATTTCAT TTTGGGGCTC TAAATGCAAT ACAATGTCTT GCAATGTTGC        60

TTA        63

SANDWICH HYBRIDIZATION ASSAYS USING VERY SHORT CAPTURE PROBES NONCOVALENTLY BOUND TO A HYDROPHOBIC SUPPORT

This is a continuation of application Ser. No. 07/834,543, filed on Apr. 10, 1992, abandoned.

BACKGROUND OF THE INVENTION

1. Technical Field

The present invention concerns a procedure for detection of a single-stranded nucleotide sequence in a specimen containing it or potentially containing it, by implementing the sandwich hybridization technique. This procedure is applicable, in particular, to the diagnosis of infectious or genetic diseases and to cell typing.

2. Background Information

It is known that one of the characteristic properties of nucleic acids is their ability to interact with a complementary sequence by means of hydrogen bonds and thus, to form a stable hybrid in accordance with the laws of pairing A-T and G-C.

Thus, a nucleic acid may be used as a probe to reveal the presence, in a specimen, of a nucleic sequence (termed "target") containing a sequence complementary to the sequence in the probe. Marking of the hybrid combining the target and the probe makes possible the detection and quantification of the target in the sample. This technique has been used by E. M. Southern to analyze DNA fragments after electrophoresis gel separation (*J. MOL. BIOL.* 98, 503 (1975).

A modification of this technique, which gives the advantage of not requiring purification of the target-containing sample, consists in the use of a "sandwich" protocol. A first nucleotide probe (capture probe) attached to a solid support is used to capture the gene or gene fragment in the sample. A second probe (detection probe), complementary to another region of the target, allows detection by means of a marker, such as a radioactive marker (see, for example, A. R. Dunn and J. A. Hassel, *J.A. CELL*, 12, 23, (1977); M. Ranke et al., *GENE*, 21, 77 (1983); A. Palva et al., *FEMS MICROBIOL. LETT.*, 23, 83 (1984) and R. Polsky-Cynkin et al., *CLIN. CHEM.*, 31, 1438 (1985).

The sandwich hybridization method may be implemented by adding, in a single step, the specimen to be analyzed and the detection probe in a container in which the capture probe is attached to the support. In this case, the hybridization method used is termed "simultaneous"; (see, for example, the aforementioned articles by Ranke et al, Palva et al, and Polsky-Cynkin et al.).

The sandwich hybridization technique may also be carried out in two stages (see, for example, J. A. Langdale et al., *GENE* 36 201 (1985) and J. W. Zolg et al., *MOL BIOCHEM. PARASITE* 22, 145 (1987).

To permit use of these hybridization techniques in routine tests, radioactive marking of the detection probe must be dispensed with. To this end, various systems utilizing a hapten recognized by an antibody or by an affine protein have been suggested. In particular, various DNA or RNA marking methods using biotin or its derivatives have been proposed; see especially European Patent Application 0285057, 0285058, 0286898, and 0097373; Forster et al., *NUCLEIC ACID RES.*, 13, 745 (1985); A. Chollet and R. H. Kawashima, *NUCLEIC ACID RES.*, 13, 1529 (1985); B. C. Chin et al., *NUCLEIC ACID RES.*, 11, 6513 (1983); A. J. Cocuzza, *TETRAHEDRON LETT.*, 30, 6287 (1989). However, the detection systems utilizing non-radioactive marking methods lack sensitivity (see, for example, Zolg et al., article cited above).

Furthermore, the diagnosis of genetic diseases, cell typing, and even, in some cases, the identification of mutant viruses require the detection of site-specific mutations in the genome. In these cases, the perfection of capture probes whose sensitivity is sufficient to detect a site-specific mutation in the area of the target complementary to the sequence to the capture probe proves difficult. The probe systems currently on the market to perform this kind of detection are not highly practical, since each commercial system must be implemented at a given temperature which varies depending on the system used, thereby preventing varied analyses on automatic equipment which operates at a single temperature.

SUMMARY OF THE INVENTION

The purpose of the present invention is a procedure for detection of nucleic sequences by implementing sandwich hybridization, said procedure being sufficiently sensitive to allow the use of a non-radioactive detection probe. This objective can be achieved by virtue of the use of very short capture probes which, it has been discovered, impart a high degree of specificity to the sandwich test while preserving a high degree of sensitivity, and which make it possible to detect and differentiate sequences homologous to within one nucleotide. The use of short oligonucleotides facilitates formation of large quantities of probes giving acceptable yields and makes it possible to obtain a wide range of selectivities. This is particularly useful in the case of HLA typing, where mutations specifying the cell type are localized on short portions of the gene.

It has been discovered, furthermore, that it is possible to produce direct, passive adsorption of very short oligonucleotides (up to a minimum of 11 nucleotides) on a polymer support, such as polystyrene, and to obtain the passive fixation of even shorter probes (minimum of 9 nucleotides) by means of a protein to which the probe is covalently linked. This is a surprising result, since, until now, use was generally made, as capture probes, of sequences comprising more than 100 bases (normally several hundreds of bases); and since, also, the oligonucleotide sequences $(dT)_{15}$ do not bond passively (i.e., by adsorption) on the polystyrene (see M. L. Lacy and K. W. Voss, *J. OF IMMUNOL. METHODS*, 116, 87–98 (1989) Other authors sought to promote bonding of the capture probe by saturating the polystyrene support with $poly(dT)_{4000}$ and by coupling the capture probe, comprising several tens of bases,to a "tail" made of poly(dA) containing from 30 to more than 100 units (see D. V. Morrissey and M. L. Collins, *MOLECULAR AND CELLULAR PROBES*, 3, 1, 89–207 (1989). In Applicant's experience, saturation of the solid support using poly(dT) does not improve detection.

Furthermore, by virtue of the use of short probes giving increased sensitivity, the procedure according to the invention makes it possible to choose, as desired, a predetermined working temperature and to construct, in each case, probes whose length is suited to the conduct of analyses of the most diverse targets at a single predetermined working temperature. The simplification of the procedure and the resulting opportunities for automation will be easily acknowledged.

DETAILED DESCRIPTION OF THE INVENTION

Figure 1:
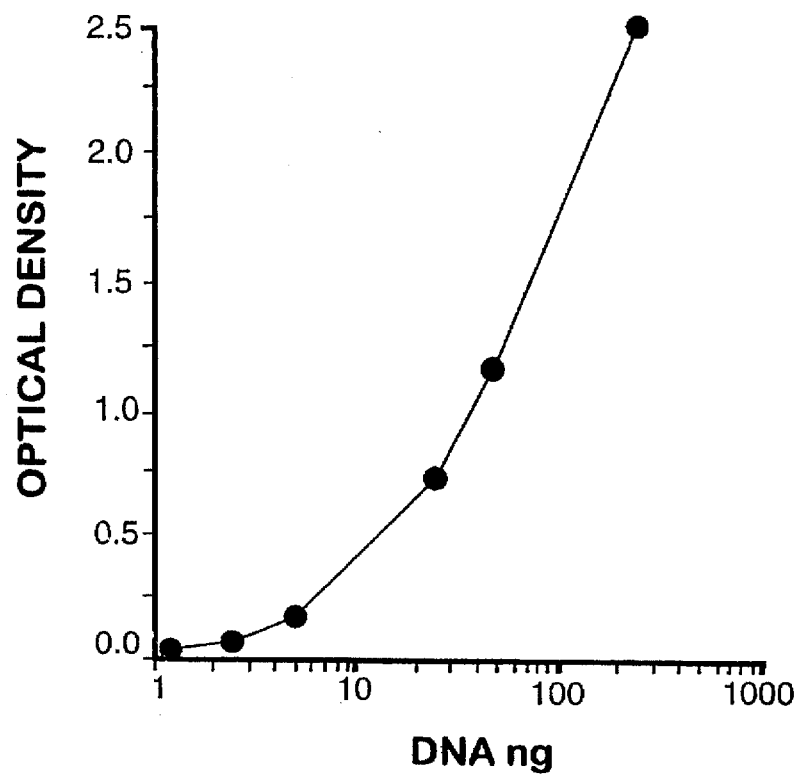
FIG. 1 Results of DNA detection (Tem) after amplification, related to Example 10.

Thus, the purpose of the present invention is a procedure for detection of a single-stranded nucleotide sequence in a specimen containing it or capable of containing it, by implementing the sandwich hybridization technique using a capture probe passively fixed on a solid support and a detection probe marked with a non-radioactive marker, the capture and detection probes being capable of hybridization, respectively, with two non-overlapping areas of the nucleotide target sequence sought, characterized by the fact that the capture probe, which contains from 9 to 30 nucleotides, and in particular, from 9 to 25 nucleotides is passively fixed on said solid support made of a hydrophobic material.

When the capture probe contains at least 11 nucleotides, it is normally possible to fix it non-specifically (i.e., by means of adsorption) on the support, which is generally made of a hydrophobic polymer such as polystyrene or a styrene-based copolymer, in particular a butadiene-styrene or analogous copolymer. Among the possible styrene copolymers, mention is made of those which contain at 10% by weight of styrene units, and in particular, those which contain at least 30% by weight of styrene units. The material used to make the solid support used according to the invention may, furthermore, be made of a mixture of a polystyrene and/or a styrene copolymer (especially butadiene-styrene) with another polymer making it possible, in particular, to improve the properties of the sold support (mechanical properties, transparency, etc.). Said other polymer is, for example, a styrene-acrylonitrile or methyl styrene-methacrylate polymer, a polypropylene, or a polycarbonate or similar polymer. The polymer mixture composing the solid support then contains at least 10% by weight, and preferably at least 30% by weight, of styrene units. As the solid support, use may be made of a conical support marketed by Vitek (USA) and produced using a butadiene-styrene copolymer material, such as that sold under the tradename K-Resin.

It is also possible, and when the capture probe is very short in particular with less than 11 nucleotides, it even becomes a necessity, to implement means allowing improved fixation of the capture probe on the solid support. As previously indicated, the capture probe may, for example, be covalently linked, using conventional methods, to a protein which is itself passively fixed on the support, which is made from the aforementioned substances). Of course, the protein promoting fixation of the capture probe must not interfere with detection. For example, when the detection probe is marked with an enzyme, the protein fixed on the solid support must produce no enzymatic interference activity. Among the proteins which can be used for the passive, indirect fixation of the capture probe on the support, mention may be made of mammal albumin (e.g., bovine albumin) or a bacterial proteinic toxin, such as tetanic toxin. A protein and/or a coupling method making it possible to fix one or two molecules of the capture probe per molecule of protein will preferably be selected.

The coupling between the oligonucleotide and the protein may occur, for example, by means of an alkylene branch having 3 to 12 carbon atoms, which can be added to the end 5' of the oligonucleotide making up the capture probe,during automatic synthesis. This branch supports a primary amine function which, after activation and by virtue of a homobifunctional coupling agent such as DITC(phenylene-1,4-diisothiocyanate, DSS (disuccinimidyl suberate) or DIBS(-4,4-diisothiocyanostilbene-2,2'-disulionicacid) allow grafting onto the $NH_2$ functions borne by the lysines of the albumin. The conjugate is purified by high-performance liquid chromatography on an ion-exchange column. It was found that passive fixation of the capture probe by means of a protein, as described above, prove quite advantageous, especially because it supplies results which have a high capability of replication.

The detection probe may itself be a short probe containing 9 to 30 nucleotides. However, to ensure the desired specificity, the detection probe preferably contains at least 15 nucleotides, e.g., 15 to 30 nucleotides, when the capture probe is very short and contains, in particular, fewer than 15 nucleotides. The detection probe is covalently coupled with a non-radioactive market, e.g., an enzyme. Covalent coupling is performed using conventional methods, especially using the method described above for coupling an oligonucleotide constituting the capture probe and a protein. As enzymatic marker, use may be made of a peroxidase, such as horseradish peroxidase, an alkaline phosphatase, an acid phosphatase, beta-galactosidase, glucose oxidase, etc.

Of course, to produce capture and detection probes, the sequence, or part of the sequence of the target must be known; alternatively,the sequence or a part of the sequence of the protein coded for the target must be known. The oligonucleotides constituting the probes can then be synthesized using an automatic DNA-synthesis apparatus, such as models 380 and 381 marketed by Applied Biosystems.

The capture and/or detection probes may be composed of DNA or RNA.

Furthermore, the probes used according to the invention may contain, or be composed of, alpha-nucleotides analogous to natural nucleotides (see, in particular, French Patent 2 607 507). The alpha-nucleotides may be produced on automatic synthesizers. They can be derived at ends 3' or 5' and are coupled to the proteins in the same manner as the beta-oligonucleotides. They have the advantage of good stability with respect to nucleases (see N. T. Thuong et al., PROC. NAT. ACAD. SCI., USA, 84,5179 (1979). The alpha-oligonucleotide-enzymes conjugates are more stable in solution than the beta analogues, and can be stored longer at lower dilutions.

The nucleic acid to be detected (target) may be double-stranded DNA, single-stranded DNA, a DNA-RNA hybrid, or RNA (ribosomal or messenger). Of course, in the case of a double-stranded nucleic target or of a DNA-RNA hybrid, it should be denatured before implementing the detection procedure using the sandwich hybridization technique. Double-stranded DNA may itself be obtained after the extraction, using conventional methods, of nucleic acids from a sample to be analyzed. This extraction can be performed by cell proteolysis, followed by phenol-chloroform extraction (see, for example, Maniatis et al., "Molecular Cloning: A Laboratory Manual," Cold Spring Harbor Laboratory, New York (1982); or, in more direct fashion, by alkaline treatment in the presence of detergent and/or by ultrasound treatment, or using any other procedure which release nucleic acids in the liquid phase. The sample to be treated may contain a mixture of cells, bacteria, yeasts, viruses, or other microorganisms. The double-stranded DNA thus obtained may be used directly, after denaturation implementing conventional techniques, or it can be used as a matrix for the amplification of nucleic acids, in order to obtain quantities sufficient for their detection.

To obtain the single-stranded form from an RNA-DNA hybrid or from a double-stranded DNA, physical, chemical, or enzymatic denaturation may be performed. One physical denaturation method consists in the separation of the two strands by heating the hybrid until it is completely denatured, e.g., at a temperature of 80° to 105° C. for a period of several seconds to several minutes. The chemical denaturation method consists, for example, in placing the double-stranded sample in contact with a 0.2M sodium hydroxide solution for 10 minutes, this treatment being followed by neutralization using acetic acid at the same concentration (0.2M), until a pH of between 6 and 8 is reached. One enzymatic denaturation method consists in the use of a helicase. Techniques utilizing helicases are described notably by Radding, *ANN. REV. GENETICS*, 16, 405–437 (1982). Other enzymes having the same function can be used for the same purpose.

The procedure according to the invention is preferably carried out using the simultaneous method.

This method involves:

the passive fixation of the oligonucleotide capture probe on the solid support, either directly or by means of a protein, as previously described. The support is placed in contact with an aqueous solution containing the probe;

the rinsing of the support and drying, as needed to preserve it;

the support thus obtained is placed simultaneously in contact with a solution containing the sample to be analyzed and with a solution containing the marked oligonucleotide detection probe, and the sample and the detection probe can be added either as a mixture or separately;

the incubation of the mixture obtained;

the rinsing of the support to eliminate the constituents not fixed on the support by means of hybridization; and the qualitative or quantitative detection, using a disclosure reaction revealing the marker fixed on the support, e.g., by colorimetry, fluorescence or luminescence.

A specific, non-limiting embodiment of implementation of the procedure according to the invention will be given below.

1. Fixation of the Capture Probe

The capture probe is fixed by depositing in each well, for example, 100 μl of a microtitration plate of a solution containing 0.1 μg/ml to 10 μg/ml of oligonucleotides, and preferably 1 μg/ml, in solution in a PHS 3X buffer (0.45M NaC, 0.15M sodium phosphate, pH=7.0).

The plate is left in contact with the capture probe solution for at least 2 hours at 37° C., then washed using a PBS IX solution (150 mM NaCl, 50 mM sodium phosphate buffer, pH=7,0, containing 0.5% Tween 20).

2. Simultaneous Incubation of the Samples and of the Marked Detection Probe

After undergoing the denaturation treatment, if necessary, the samples (target) are deposited on the plate as a solution in the PBS 3X buffer containing heterologous DNA, e.g., salmon sperm DNA in a concentration of 10 μg/ml.

The marked probe is diluted in the aforementioned buffer in a concentration of 20 to 100 μg/ml. 50 μl of this solution is placed in the well containing the target.

The microtitration plate is then incubated for a period ranging, for example, from 30 to 120 minutes at the temperature selected, e.g. 37° C., or for a shorter period if a lower sensitivity is required.

3. Washing

Washing is carried out using, for example, PBS IX buffer containing 0.5% Tween 20 (Merk 82 21 84).

4. Enzymatic Tracing

Tracing is performed with the substrate corresponding to the enzyme used. For example, orthophenylene diamine (OPD) can be added when the marker is the horseradish peroxidase or paranitrophenylphosphate (PNPP) or methyl-5 umbelliferylphosphate (MUP), when the marker is alkaline phosphatase.

The tracing time of the substrate normally ranges between 1 and 30 minutes, after which the reaction is halted by adding 1N NaOh in the case of alkaline phosphatase, or 1N $H_2SO_4$ in the case of horseradish peroxidase.

Reading is performed on a microplate reader at 405 nm for PNPP, 492 nm for OPD, and under fluorescence for MUP (excitation 340 nm, emission 460 nm).

The consecutive incubation and washing stages, which constitute key steps in the sandwich hybridization process, will be discussed below. These incubation and washing operations are each performed at a constant temperature of between 20° and 60° C., and preferably between 25° and 40° C. One of the advantages of the use of short probes is to allow the sandwich tests in order to detect different targets while performing these different analyses at a single predetermined temperature, which will be preferably 37° C. all laboratories are equipped with thermostat-equipped equipment set to that temperature.

It is known that DNA hybrids have a dissociation temperature which depends on the number of hybridized bases (the temperature increasing as the size of the hybrid increases) and which also depends on the nature of these bases and, for each hybridized base, on the nature of the adjacent bases.

Hybrid dissociation occurs over a range of several ° C. and can be easily determined using UV spectroscopy. In fact, the optical density of the hybrid is lower than that of corresponding single-stranded sequences. It thus proves possible to determine, in each case, a half-dissociation temperature characteristic of the hybrid under study.

Knowledge of the reaction entropy and enthalpy make it possible, moreover, to compute (Van't Hoff's Law) the half-dissociation temperature of a given hybrid under standard conditions (e.g., in a saline solution corresponding to 1M NaCl) as a function of the total concentration of nucleic acid in the solution (see, for example, K. L. Breslauer et al., *PNAS*, 83, 3476 (1986); W. Rychlik and R. E. Rhoads, *NUCLEIC ACID RES.*, 17, 8543 (1989); and S. M. Freier et al., *PNAS*, 83 9373 (1986).

In practice, it is still possible to determine the half-dissociation temperature of the hybrid formed by a given probe and the target having a complementary sequence, by simple routine experiments.

The hybridization temperature of the sandwich protocol (incubation temperature and/or washing temperature) must obviously be chosen so as be below the half-dissociation temperature; if not, the target will not hybridize with the capture and/or detection probe, and the test results will be erroneous.

It is understood that these remarks concerning the half-dissociation temperature relate to the less stable (i.e., the hybrid having the lower half-dissociation temperature) of the two hybrids which the target forms with the capture probe, on the one hand, and with the detection probe, on the other. In fact, to enable the sandwich protocol to work correctly, it is obviously required that, when a positive result is sought, these two hybrids be stable at the working temperature.

A site-specific mutation leading to a mispairing affecting a single pair of bases in the hybrid entails a modification, normally a lowering, of the half-dissociation temperature.

One basic advantage resulting for the use of short probes lies in the fact that a single mispairing of this kind can lead to a relatively significant reduction of the half-dissociation temperature, i.e., of approximately 2° to 4° C. This does not occur with long probes, in which a single mispairing of this type lead only to a very slight variation of the half-dissociation temperature.

It has now been discovered that it is possible to profit from the use of short probes to conduct analyses according to the sandwich protocol at a single predetermined temperature, e.g., 37° C., as previously indicated.

In the following description, the reasoning will be based, as an example, on the generally preferred case in which it is the capture probe which produces, in conjunction with the target sought, a hybrid which is less stable than target/detection probe hybrid. However, it is obvious that use may also be made of a system in which, inversely, it is the detection probe/target hybrid which is less stable (in the following description, one need only replace the expression "capture probe" by "probe, in conjunction with the target, gives the less stable hybrid" to adapt this reasoning to the most general case).

Of course, the capture probe (as well as the detection probe) must be long enough so that the half-dissociation temperature is greater than the temperature selected. If one wishes to conduct a very sensitive test (in particular, a test sensitive to a single mutation), use should be made of an adjusted capture probe (and/or detection probe), i.e., a probe whose length is sufficiently short and whose sequence is such that the half-dissociation temperature is only slightly greater than the predetermined hybridization temperature, the gap between the two temperatures being, for example, 1° to 3° C., since, at this stage, work should proceed at the maximum allowable temperature to avoid non-specific hybridizations, which would be possible by using a temperature which is too low in relation to the dissociation temperature of the completely complementary hybrid. In fact, the allowing temperature variation can be determined, in each case, by simple experiments.

In the case just described, at the hybridization temperature thus set, only a target completely homologous to the capture probe will remain fixed on the probe, while a target comprising a site-specific mutation in the region complementary to the probe will not be fixed.

In the preceding discussion, special emphasis was placed on the choice of a capture probe adapted to the hybridization temperature chosen, mainly by means of adjustments made to the size of the probe. However, it is obvious that specialists can also vary the choice of the probe sequence, since the half-dissociation temperature may vary as a function of the nature of the bases involved in hybrid formation. It is also possible to change the hybridization conditions, and, in particular, the saline concentration of the incubation solution and/or of the solution used for washing subsequent to incubation. It is known, in fact, that the increase of the saline concentration leads to an increase of the half-dissociation temperature.

In the practical implementation of the invention procedure, when using a capture probe and/or hybridization conditions adapted to the predetermined temperature selected, the procedure may be carried out in two ways.

According to a first embodiment, the incubation phase is effected at said predetermined temperature and the washing step is performed at said temperature or at a lower temperature. This embodiment is made possible since, at the working temperature, only a target complete homologous to the capture probe can be hybridized, with the result that there is no risk of fixation of a target which is not perfectly homologous, even were the washing to be performed at a temperature lower than the incubation temperature.

According to a second embodiment, incubation is conducted at a temperature below said predetermined temperature, and washing is carried out at said predetermined temperature. In fact, in this case the washing temperature will be discriminating, and any hybrid that may be formed at the incubation temperature between the capture probe and a target not completely homologous will no longer be stable at the washing temperature and will thus not remain fixed on the support.

To detect a site-specific mutation, one may proceed in two ways.

Either the capture probe contains the mutation complementary to the mutation sought, in which case the mutated target will be hybridized under the conditions of the hybridization test;

or the capture probe is completely homologous to the sequence complementary to the non-mutated target, in which case only the non-mutated target will hybridize.

The procedure according to the invention is particularly applicable:

to the detection of the DNA or virus-messenger RNA, or of the retrovirus RNA;

to the analysis of the DNA, the messenger or ribosomal RNA, and the DNA-RNA hybrids of bacteria, parasites, and yeasts;

and to the analysis of vertebrate DNA, in particular of human DNA, in order to perform HLA typing or for detecting genetic diseases (myopathy, diabetes, fibrocystic disease, etc.).

The following examples illustrate the invention without, however, limiting it.

In these examples, in accordance with the convention generally applied, the nucleotide sequences are represented with the end 5' to the left.

The invention also concerns the use of the probes described in the examples for the detection of the target indicated. It must be understood that the probes mentioned in the examples must be considered to be minimum sequences which could be elongated (within the indicated limits of a maximum of 30, 35, or 20 nucleotides) by addition supplementary nucleotides which are, of course, selected so that the probe is homologous to the target whose sequence is here presumed to be known. All of the probes mentioned as being satisfactory in the examples allow procedures to be carried out at 37° C.

In the example for which two sequences are given for the capture probe (or for the detection probe), this indicates that one of the probes, or both probes, can be used. The use of two capture probes and/or two detection probes makes it possible to amplify the signal when the results do not prove satisfactory using a single probe.

Figure 2:
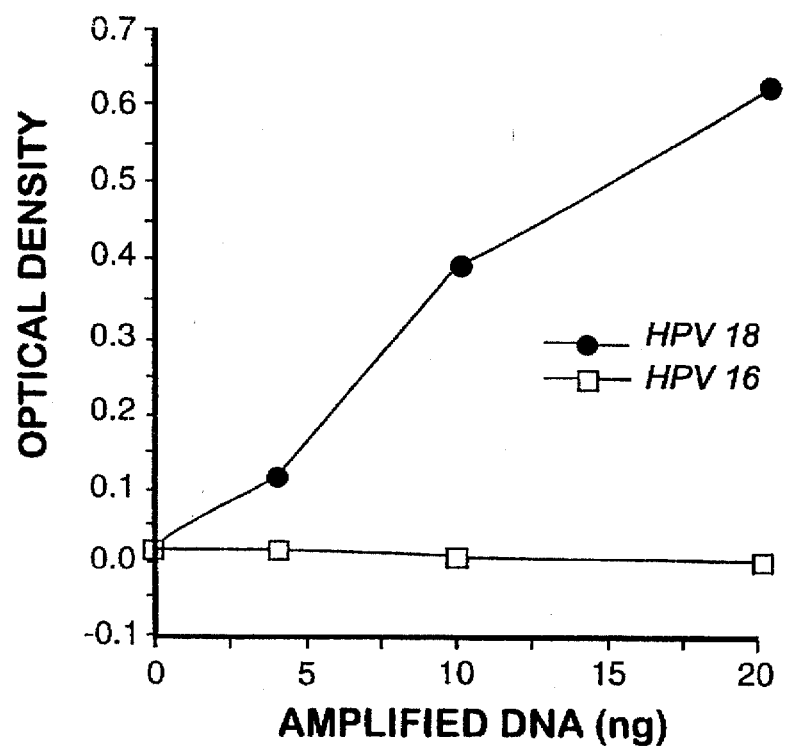
FIG. 2 Amplified DNA detection (HPV18) by oligonucleotide-peroxidase, revealing that HPV 18 is detected while HPV is not.

The references to FIGS. 1 and 2, attached, are provided in Examples 10 and 15, respectively.

EXAMPLE 1

Preparation of the phosphoramidite branch for the addition of an $NH_2$ branch at position 5' of an oligonucleotide:

21.0 g (0.2 mole) of amine-5 pentanol-1 (Aldrich 12304-8) were dissolved in 90 ml of THI, and 5.3 g of $Na_2CO_3$ were added. The mixture was cooled to −5° C., and 14 g (0.67 mole) of trifluoracetic anhydride (Aldrich 10623-2) dissolved in 50 ml of THF was dripped into the mixture for 1 hour.

The mixture was stirred for 1 hour at ambient temperature. After filtration and evaporation of the THF, the product was vacuum-distilled. The fraction $E_{0.3}$ mm=79°–90° C. was collected and purified on a silica gel using a mixture of $CH_2Cl_2$, MeOH 80:20.

The desired product had an Rf of 0.6. Yield was 66%.

0.7 g of protected amino-alcohol (3.48 $10^{-3}$ mole) was dried with pyridine (2×3 ml) with 3 ml of N-ethyldiisopropylamine (13.92 $10^{-3}$ mole) and dissolved in 15 ml of $CH_2Cl_2$. 1.65 g (6.96 10–3 mole of cyanoethyl-2-N,N-diisopropylchlorophosphoramidite (Aldrich 30230-9) were added under argon at ambient temperature for 35 mn. 0.2 ml of MeOH and, after stirring for 10 mn, 30 ml of ethyl acetate, were added. The organic phase was cold washed using twice 60 ml of 10% $Na_2CO_3$, then 2×80 ml of saturated NaCl, dried on $Na_2SO_4$, then evaporated using a rotary evaporator.

The unpurified product was purified on a silica column in a mixture of ethyl acetate $CH_2Cl_2$-$NEt_3$ (45-45-10). The fraction collected (Rf=0.75) was concentrated in the rotary evaporator and stored under argon.

The oligonucleotide was synthesized on an Applied 381A automatic apparatus using phosphoramidite chemistry. The phosphoramidite branch, dissolved in anhydrous acetonitrile in an 0.2 molar concentration, was placed in position X of the synthesizer. The branch was added implementing the standard end-of-synthesis protocol. After overnight deprotection at 55° C. in 33% $NH_4OH$ and precipitation in ethanol at 20° C., the oligonucleotide was vacuum-dried and replaced in 1 ml water. $3.10^{-8}$ moles of oligonucleotide were vacuum-dried and replaced in 25 µl of a 0.1M sodium borate buffer, pH=9.3. 500 µl of a 30 mg/ml solution of DICT (Fluka 78480) in DMF were added. The mixture was stirred for 1 h 30 mn at ambient temperature before adding 3 ml of $H_2O$. After extraction of the solution using butanol (3×3 ml), the remaining aqueous phase (500 µl) was vacuum-dried, then recovered using $1.10^{-7}$ mole (6.6 mg) of BSA (Pierce 30444) in 200 µl of borate buffer. After stirring overnight at ambient temperature, the conjugate was purified by ion-exchange in CLHP on an AX300 column (Brownlee 4.6× 100 mm) by means of an NaCl gradient (Table 1, including SEQ ID NOS:7, 15, 9, 10, 11 and 12, respectively). The conjugate peak was dialyzed against water (2×1 liter), concentrated in a vacuum, recovered in 1 ml $H_2O$, then stored at −20° C.

TABLE I

| LENGTH | OLIGONUCLEOTIDE | Tr min. | mM NaCl | Ratio oligo/ ASB |
|---|---|---|---|---|
| 20 | 5'-AACGCTACTACTATTAGTAG-3' | 11.96 (2M) | 603 | 1.0 |
| 15 | 5'-TTGCATTTAGAGCCC-3' | 15.50 (1M) | 395 | 1.4 |
| 13 | 5'-TGCATTTAGAGCC-3' | 15.47 (1M) | 385 | 1.1 |
| 12 | 5'-GCATTTAGAGCC-3' | 14.49 (1M) | 367 | 1.6 |
| 11 | 5'-GCATTTAGAGC-3' | 14.41 (1M) | 365 | 1.2 |
| 9 | 5'-CATTTAGAG-3' | 13.99 (1M) | 356 | 1.1 |

Tr = retention time as a function of the NaCl concentration.
The elution gradient is from 10% to 56% of buffer B in 25 minutes, where Buffer A = 20 mM sodium phosphate buffer, pH = 7,00, and buffer B = buffer A containing 2M (or 1M) NaCl.

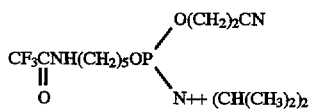

EXAMPLE 2

Preparation of an ASB oligonucleotide conjugate:

EXAMPLE 3

Preparation of a horseradish peroxidase oligonucleotide:

In accordance with Example 2, the activated, vacuum-dried oligonucleotide was recovered using $1.25\ 10^{-7}$ mole (5 mg of horseradish peroxidase) (Boehringer 413470) in 200 µl of borate buffer.

The purification protocol was identical: the conjugate was stored at −20° C. in a 50 mM tris HCL, pH=7.0, 40% glycerol buffer. The results are given in Table 2.

TABLE 2

| TYPE | SEQUENCE 5'→3' | Tr min mM NaCl | | Ratio oligo/HRP |
|---|---|---|---|---|
| TEM | TGCCATAACCATGAGTG | 22,26 (1M) | 491 | 1,1 |
| TEM | ATAACACTGCGGCCAAC | 20,01 (1M) | 450 | 1,0 |
| TEM | GTTGGCCGCAGTGTTAT | 11,03 (2M) | 569 | 1,5 |
| TEM | CACTCATGGTTATGGCA | 11,45 (2M) | 585 | 1,3 |
| B GLUCURONIDASE | GATCGCGGTGTCAGTTCTTT | 11,85 (2M) | 599 | 1,5 |
| B GLUCURONIDASE | TTCCATGGGTTTCTCACAGA | 11,83 (2M) | 600 | 1,1 |
| B GLOBINE | GTATCATGCCTCTTTGCACC | 11,57 (2M) | 590 | 1,0 |
| B GLOBINE | TTTCTGGGTTAAGGCAATAGC | 11,82 (2M) | 600 | 1,1 |
| RAS | TTCCTCTGTGTATTTGCCAT | 22,99 (1M) | 505 | 1,0 |
| RAS | ACATGAGGACAGGCGAAGGC | 20,97 (1M) | 467 | 1,1 |
| C. TRACHOMATIS | AATCCTGGCTGAACCAAGCCT | 20,70 (1M) | 462 | 1,0 |

TABLE 2-continued

| TYPE | SEQUENCE 5'→3' | Tr min mM NaCl | | Ratio oligo/HRP |
|---|---|---|---|---|
| C. TRACHOMATIS | AAGGTTTCGGCGGAGATCCT | 19,30 (1M) | 437 | 1,0 |
| HIV 1-2 GAG | GAAGCTGCAGAATGGGA | 9,18 (2M) | 501 | 1,3 |
| HIV 1 ENV | AACAATTGCTGAGGGCTAT | 25,19 (1M) | 545 | 1,0 |
| HIV 2 ENV | GGTCAAGAGACAACAAGAA | 9,19 (2M) | 501 | 1,4 |
| HIV 1 POL | GCCTGTTGGTGGGC | 9,56 (2M) | 515 | 1,0 |
| HLA DR | CCGGGCGGTGAC(G/T)GAGCTGGGGC | 12,31 (2M) | 616 | 1,3 |
| HLA DR | GAACAGCCAGAAGGAC | 9,84 (2M) | 525 | 1,0 |
| HLA DQ | GGCGGCCTGATGCCGAGTAC | 10,16 (2M) | 537 | 1,1 |
| HPV 6/11 | GACCCTGTAGGGTTACATT | 10,20 (2M) | 539 | 1,0 |
| HPV 6/11 | TGACCTGTTGCTGTGGA | 9,91 (2M) | 528 | 1,0 |
| HPV 16 | CCGGACAGAGCCCATTAC | 11,33 (2M) | 580 | 1,1 |
| HPV 16 | CTCTACGCTTCGGTTGTGC | 11,65 (2M) | 592 | 1,0 |
| HPV 18 | GTATTGCATTTAGAGCCCCA | 13,07 (2M) | 644 | 1,1 |
| HPV 18 | TAAGGCAACATTGCAAGACA | 11,16 (2M) | 574 | 1,1 |
| alpha HPV 18 | ACCCCGAGATTTACGTTATGT | 10,80 (2M) | 560 | 1,0 |

Tr = time of retention (minutes) as a function of the saline concentration (1M or 2M).
Gradient conditions are identical to those described in Example 2. each DNA sequence in Table 2 is represented in SEQ ID NOS:21, 22, 17, 18, 78, 79, 84, 85, 90, 105, 54, 55, 109, 65, 69, 73, 13, 104, 6, 52, 29, 106, 42, 43, 48, 49, and 4, respectively.

EXAMPLE 4

Preparation of an alkaline phosphatase oligonucleotide conjugate:

Following Example 2, the activated, vacuum-dried oligonucleotide was recovered using 5.7 $10^{-8}$ mole (8.0 mg) alkaline phosphatase (Boehringer 567752) in manufacturer's buffer.

The purification protocol was identical (Table 3, including SEQ ID NO:48, 49 and 82, respectively). The conjugate was stored at +4° C. in a buffer containing Tris HCl 30 mM, 1M NaCl, 1 mM mgCl$_2$, pH=8.0.

TABLE 3

| DNA TYPE | OLIGONUCLEOTIDE | Tr min | mM NaCl | Ratio oligo/enzyme |
|---|---|---|---|---|
| HPV18 | 5'-GTATTGCATTTAGAGCCCCA-3' | 9.53 (2M) | 550 | 1.6 |
| HPV18 | 5'-TAAGGCAACATTGCAAGACA-3' | 13.04 (2M) | 600 | 1.4 |
| HPV18/33 | 5'-GTCCAATGCCAGGTGGATGA-3' | 10.10 (2M) | 572 | 1.0 |

Tr = time of retention (minutes as a function of the saline gradient.
Gradient conditions are identical to those in Example 2.

EXAMPLE 5

Detection of a nucleic acid sequence applying the sandwich protocol.

A 1 ng/µl (0.15 µM) oligonucleotide solution (see SEQ ID NO:92) 5'-TCAGAGGAAGAAAACGATGA-3' in PBS 3X (0.45M NaCl 0.15M sodium phosphate, pH=7.0) is deposited in a polystyrene microtitration plate (Nunc 439454). The plate was incubated for 2 hours at 37° C.

After 3 washings using 300 µl if PBS Tween (0.15M NaCl, 0.05M sodium phosphate, pH=7.0, PBS Tween 20 (Merck 822184), 50 µl of the sequence (see SEQ ID NO:2) (5'  A A G G T C A A C C G G A A T T T C A T T T T G G G G C T C T A A A T G CAATACAATGTCTTGCAATGTTGCCTTA-3') at different concentrations ranging from 100 pg/µl (5 nM) to 0.01 pg/µl (0.5 pM) in PBS salmon buffer (PBS3X+10 µg/ml (Sigma D9156) salmon sperm DNA were added in the wells, followed by 50 µlm of a solution containing the peroxidase oligonucleotide conjugate in an oligonucleotide concentration of 0.1 ng/µl (15 nM) in a PBS horse buffer (PBS3X+ 10% horse serum (BioMérieux 55842). The plate was incubated for 1 hour at 37° C. and washed three times in 300 µl of PBS Tween. 100 µl OPD substrate (orthophenylenediamine, Cambridge Medical Biotechnology ref/ 456) in an OPD buffer (0.05M citric acid, 0.1M Na$_2$HPO$_4$, pH=4.93) in a concentration of 4 mg/ml, to which was added extemporaneously 30 volumes of 1/1000 H$_2$O$_2$, were added per well. After a reaction time of 20 mn, enzymatic activity was blocked using 100 µl of I$_2$SO$_4$, and reading was performed on an Axia Microreader (BioMérieux) at 492 nm.

Sensitivity: Table 4.

TABLE 4

| | target (pg) | | | | | | | |
|---|---|---|---|---|---|---|---|---|
| | 5000 | 1000 | 500 | 100 | 50 | 2 | 0.1 | 0 |
| DO value | >2.5 | 1.007 | 0.559 | 0.136 | 0.067 | 0.028 | 0.006 | 0.005 |

DO = Optical Density

The detection limit is 2 pg of the target, or $10^{-17}$ mole.

The system is absolutely specific, since the well containing the salmon DNA, in the form of a single strand, is not detected (wells containing 0 pg/µl of target).

EXAMPLE 6

As demonstrated for sickle-cell anemia or tumor formations (in *Human Genetic Diseases: A Practical Approach*, K. E. Davies, ed., IRL Press, 1986), site-specific mutations at specific positions on the gene are responsible for genetic diseases and may be detected by hybridization of the genomic DNA using nucleic probes. Under certain conditions, a mispairing of a base may destabilize a DNA-oligonucleotide hybrid. Thus, R. B. Wallace et al. (*Nucl. Acid Res.*, 6, 3543, 1979) detected an am-3 mutation (A-C for the mutated gene in place of C-G for the normal gene) on the gene of the X174 bacteriophage using a direct hybridization system incorporating filter.

Later work demonstrated that the mutations were not equivalent from the standpoint of the destabilization of a hybrid. Thus, F. Aboubela et al. (*Nucl. Acid Res.*, 13, 4811, 1985) found that mispairings containing a guanine (GT-GG-GA) are less destabilizing than mispairings containing a cytosine (CA-CC) or a mispairing between 2 pyrimidines (TT-CC-TC).

S. Ikuta et al. (*Nucl. Acid Rest*, 15, v 797, 1987) showed that the mispairings GT and GA are less destabilizing than AA, TT, CT, or CA.

The example describes a method for detection of a completely homologous DNA using a sandwich protocol at 37° C. The capture oligonucleotides are passively fixed on the plate. The five targets chosen are described in Table 5 SEQ ID NO:113, 112, 101, 94 and 92, respectively.

TABLE 5

3'-ATTCGTTGTAACGTTCTGTAACATAACGTAAATCTCGGGGTTTTACTTT
AAGGCCAACTGGAA-5' X
3'-ATTCCGTTGTAACGTTCTGTAACATAACGTAAGTCTCGGGGTTTTACTTT
AAGGCCAACTGGAA-5' XGT
3'-ATTCCGTTGTAACGTTCTGTAACATAACGTAAAACTCGGGGTTTTACTTT
AAGGCCAACTGGAA-5' XAA
3'-ATTCCGTTGTAACGTTCTGTAACATAACGTATATCTCGGGGTTTTACTTT
AAGGCCAACTGGAA-5' XTT
3'-ATTCCGTTGTAACGTTCTGTAACATAACGTAAATATCGGGGTTTTACTTT
AAGGCCAACTGGAA-5' XAG 4 different mutations were introduced into 4 target sequences differed from the X sequence by a single mutation differed from the X sequence by a single mutation The mutations were localized in the zone 32-35 of the target. The four mispairings were of the type GT (XGT), AA (XAA), TT (XTT) and AG (XAG), and two mispairings GT and AG, which are the least destabilizing for a hybrid, were found.

The detection probe D1 5'-TAAGGCAACATTGCAAGACA-3' (see SEQ ID NO:94) was complementary in area 1-20 of the target, and was shared by all of the targets. It was marked on end 5' using peroxidase, as in Example 3.

The specificity of the system was brought about by the capture oligonucleotides (Table 6, including SEQ ID NO:107, 9, 10, 11 and 12, respectively).

TABLE 6

| OLIGONUCLEOTIDE | | Tm 1.00E–09M °C. | Tm 1.00E–08M |
|---|---|---|---|
| capture C15 | 5'-TTGCATTTAGAGCCC-3' | 59.4 | 63.8 |
| capture C13 | 5'-TGCATTTAGAGCC-3' | 49.2 | 54.2 |
| capture C12 | 5'-GCATTTAGAGCC-3' | 43.7 | 48.8 |
| capture C11 | 5'-GCATTTAGAGC-3' | 34.3 | 39.8 |
| capture C9 | 5'-CATTTAGAG-3' | 7.7 | 14.1 |

The Tm is computed under hybridization conditions, i.e., 600 mM salt for the two target molar concentrations of $10^{-8}$ and $10^{-9}$.

The five oligonucleotides have, at 5', a $C_5NH_2$ branch to allow covalent coupling on cow serum albumin (C15, C13, C12, C11, C9).

Unless specified to the contrary, the sandwich protocol was identical to that described in Example 5.

The target was deposited in a concentration of $10^{-9}$ mole/l, or 20 pg/μl (Table 7) or $10^{-8}$ mole/l, or 200 pg/μl (Table 8).

TABLE 7

| | TARGET (1.00–E09M) | | | | |
|---|---|---|---|---|---|
| | X | XGT | XAA | XTT | XAG |
| C15 | 2.390 | 0.667 | 0.061 | 0.137 | 0.234 |
| C13 | 0.405 | 0.030 | 0.005 | 0.008 | 0.018 |
| C12 | 0.271 | 0.015 | 0.003 | 0.005 | 0.007 |
| C11 | 0.100 | 0.004 | 0.004 | 0.005 | 0.005 |
| C9 | 0.005 | 0.004 | 0.005 | 0.005 | 0.005 |

Value of DO at 492 nm

TABLE 8

| | TARGET (1.00–E08 M) | | | | |
|---|---|---|---|---|---|
| | X | XGT | XAA | XTT | XAG |
| C15 | >2.5 | >2.5 | 0.211 | 0.973 | 1.328 |
| C13 | 2.320 | 0.198 | 0.010 | 0.060 | 0.081 |
| C12 | 1.500 | 0.095 | 0.005 | 0.028 | 0.032 |
| C11 | 0.610 | 0.014 | 0.003 | 0.014 | 0.008 |
| C9 | 0.002 | 0.004 | 0.003 | 0.007 | 0.003 |

Value of DO at 492 nm

The hybrid formed with the target containing a type GT mispairing is the least destabilized, and thus the most difficult to detect. The ration signal X/signal XGT may thus serve as a reference to measure the performance levels of the system (Table 9).

TABLE 9

| | RATIO X/XGT | |
|---|---|---|
| | 1.00E–08 | 1.00E–09 |
| C15 | — | 4 |
| C13 | 12 | 14 |
| C12 | 16 | 18 |

TABLE 9-continued

| | RATIO X/XGT | |
|---|---|---|
| | 1.00E−08 | 1.00E−09 |
| C11 | 44 | 25 |
| C9 | — | — |

The C12 capture oligonucleotide allows detection of any mispairing whatever on the nucleic acid sequence, while preserving for all mispairings a signal of less than 0.100 for the two concentrations and a ration X/XGT of less than 10.

EXAMPLE 7

Method of detecting a perfectly homologous DNA at 37° C.:

The capture oligonucleotides were coupled to the ASB and passively fixed on the plate.

The sandwich protocol was identical to that in Example 5.
The capture oligonucleotides were coupled to the ABS as in Example 2.

The detection probe was the same as in Example 6.
The results are given in Tables 10, 11, and 12.

TABLE 10

| | TARGET (1.00−E08 M) | | | | |
|---|---|---|---|---|---|
| | X | XGT | XAA | XTT | XAG |
| C15 | >2.5 | >2.5 | 0.390 | 1.445 | 2.139 |
| C13 | >2.5 | 0.394 | 0.025 | 0.078 | 0.092 |
| C12 | 2.319 | 0.241 | 0.016 | 0.044 | 0.056 |
| C11 | 0.763 | 0.025 | 0.006 | 0.007 | 0.009 |
| C9 | 0.010 | 0.007 | 0.005 | 0.005 | 0.006 |

Value of DO at 492 nm

TABLE 11

| | TARGET (1.00−E08 M) | | | | |
|---|---|---|---|---|---|
| | X | XGT | XAA | XTT | XAG |
| C15 | 2.421 | 1.154 | 0.080 | 0.200 | 0.364 |
| C13 | 0.050 | 0.075 | 0.015 | 0.019 | 0.024 |
| C12 | 0.423 | 0.043 | 0.007 | 0.010 | 0.013 |
| C11 | 0.134 | 0.007 | 0.007 | 0.006 | 0.009 |
| C9 | 0.006 | 0.006 | 0.007 | 0.005 | 0.009 |

Value of DO at 492 nm

TABLE 12

| | RATIO X/XGT | |
|---|---|---|
| | 1.00E−08 | 1.00E−09 |
| C15 | — | 2 |
| C13 | >6 | 7 |
| C12 | 10 | 10 |
| C11 | 31 | 19 |
| C9 | — | — |

The C11 capture nucleotide coupled to the ASB allows detection of any mispairing whatever on the nucleic acid sequence, while preserving for all mispairings a signal of less than 0.100 at both concentrations and a ratio X/XGT of less than 10.

EXAMPLE 8

Method of detecting a completely homologous DNA at different temperatures:

The detection protocol is the same as that used in Example 7.

The C11 capture oligonucleotide is coupled to the ASB and passively fixed on the plate. Target concentration is constant and established at a molar concentration of $10^{-9}$. The hybridization temperature is variable (Table 13).

TABLE 13

| TEMPERATURE °C. | X | XGT | X/XGT |
|---|---|---|---|
| 22 | 0.155 | 0.007 | 22 |
| 30 | 0.313 | 0.024 | 13 |
| 37 | 0.229 | 0.009 | 25 |
| 45 | 0.321 | 0.013 | 25 |
| 50 | 0.052 | 0.010 | 5 |

EXAMPLE 9

Method of detecting a completely homologous DNA at different temperatures:

The detection protocol is the same as that used in Example 7.

The C13 capture oligonucleotide is passively fixed directly onto the plate. Target concentration is constant and established at a molar concentration of $10^{-8}$. The hybridization temperature is variable (Table 14).

TABLE 14

| TEMPERATURE °C. | X | XGT | X/XGT |
|---|---|---|---|
| 22 | >2.5 | 0.343 | >7 |
| 30 | 2.028 | 0.337 | 6 |
| 37 | 2.281 | 0.227 | 10 |
| 45 | 1.458 | 0.134 | 11 |
| 50 | 0.653 | 0.017 | 38 |

EXAMPLE 10

Specific detection of the DNA or RNA sequence corresponding to the β-lactamase gene of *E. coli* (Tem).

When the sequence to be detected corresponds to messenger RNA, this latter is obtained either by specific purification of RNA (Maniatis et al., in *Molecular Cloning: A Laboratory Manual*, New York, Cold Spring Harbor, 1982), or by direct lysis of the bacteria after adding sodium carbonate (0.2M end) to the bacterial residue. The detection system used is complementary to the messenger RNA stranded corresponding to the TEM gene.

This system is composed of two capture oligonucleotides. Passive adsorption is carried out at a total concentration of 0.15 μM used as described in Example 5.

Detection occurs through the use of two oligonucleotides marked with peroxidase (in a total concentration of 15 nm).

The oligonucleotide sequences (SEQ ID NO:1 and SEQ ID NO:14, respectively) are as follows:

CAPTURE 1 = 5'-GCACTGCATAATTCTT-3'

CAPTURE 2 = 5'-TACTGTCATGCCATCC-3'

(see SEQ ID NO:17)

DETECTION 1 = 5'-GTTGGCCGCAGTGTTAT-3'

(see SEQ ID NO:18)

DETECTION 2 = 5'-CACTCATGGTTATGGCA-3'

Detection of purified, non-amplified RNA (Table 15):

TABLE 15

| PURIFIED RNA | DO VALUE |
| --- | --- |
| 10 µg specific RNA | 0.100 |
| 1 µg specific RNA | 0.014 |
| 10 µg specific RNA | 0.006 |

Detection of unpurified RNA colonies (Table 16):

TABLE 16

| NUMBER OF COLONIES | DO VALUE |
| --- | --- |
| 1.00E+08 specific colonies | 0.150 |
| 1.00E+07 specific colonies | 0.045 |
| 1.00E+06 specific colonies | 0.004 |
| 1.00E+05 specific colonies | 0.001 |
| 1.00E+08 non-specific colonies | 0.001 |

The detection limit of the RNA system, without amplification, is 1 µg of total purified RNA and $10^6$ to $10^7$ bacterial colonies.

When the sequence corresponds to unamplified DNA (pBR 322 plasmid containing the B lactamase gene, detection is performed directly on the denatured DNA under the conditions previously described.

The detection system used is the following one:

(see SEQ ID NO:19)
CAPTURE 1 = 5'-GGATGGCATGACAGTA-3'

(see SEQ ID NO:20)
CAPTURE 2 = 5'-AGAGAATTATGCAGTGC-3'

(see SEQ ID NO:21)
DETECTION 1 = 5'-TGCCATAACCATGAGTG-3'

(see SEQ ID NO:22)
DETECTION 2 = 5'-ATAACACTGCGGCCAAC-3'

The results are as follows (Table 17):

TABLE 17

| pBR322 DNA | DO Value |
| --- | --- |
| 1 µg | 0.130 |
| 0.1 µg | 0.012 |
| 0.01 µg | 0.002 |
| 10 µg salmon DNA | 0.002 |

The sensitivity on unamplified DNA is 0.1 µg, i.e., $3.48 \cdot 10^{-14}$ moles, the equivalent of $2.10^{10}$ true molecules.

When the DNA to be detected correspond to DNA amplified by a chain reaction using a polymerase, the oligonucleotides used as the following ones:

(see SEQ ID NO:23)
TRIGGER 1 = 5'-ATCAGCAATAACCAGC-3'

(see SEQ ID NO:24)
TRIGGER 2 = 5'-CCCCGAAGAACGTTTTC-3'

The DNA to be detected is denatured using the protocol previously mentioned. Detection is carried out using one of the two systems described in this example.

FIG. 1 gives the results obtained, representing along the abscissa the quantity of DNA (ng) and, along the ordinate, the optical density.

Sensitivity is approximately 1 ng of DNA obtained after amplification, taking into account the fact that the total DNA quantity produced after amplification is approximately 2.0 µg.

For an amplified segment containing 560 pairs of bases, the detection threshold is thus approximately $2.94 \cdot 10^{-15}$ moles, or $1.7 \cdot 10^9$ trues molecules.

EXAMPLE 11

Detection of the sequence corresponding to the E7 gene of the human type 6 papillomavirus.

When the sequence to be detected is amplified DNA, the sequences used are as follows:

(see SEQ ID NO:25)
TRIGGER 1 = 5'-TACACTGCTGGACAACATGC-3'

(see SEQ ID NO:26)
TRIGGER 2 = 5'-GTGCGCAGATGGGACACAC-3'

The DNA, whether amplified or not, can be detected using the following system (strand detection):

(see SEQ ID NO:27)
CAPTURE 1 = 5'-CAGTGTACAGAAACA-3'

(see SEQ ID NO:28)
CAPTURE 2 = 5'-GAGTGCACAGACGGA-3'

(see SEQ ID NO:29)
DETECTION 1 = 5'-GACCCTGTAGGGTTACATT-3'

(see SEQ ID NO:106)
DETECTION 2 = 5'-TGACCTGTTGCTGTGGA-3'

EXAMPLE 12

Detection of the DNA sequence corresponding to the E7 gene of the human type 11 papillomavirus.

When the sequence to be detected is amplified DNA, the sequences used are as follows:

(see SEQ ID NO:30)
TRIGGER 1 = 5'-TACACTGCTGGACAACATGC-3'

(see SEQ ID NO:31)
TRIGGER 2 = 5'-GTGCGCAGATGGGACACAC-3'

The DNA, whether amplified or not, may be detected using the following system (strand detection):

(see SEQ ID NO:32)
CAPTURE 1 = 5'-GAGTGCACAGACGGA-3'

(see SEQ ID NO:33)
CAPTURE 2 = 5'-CAACTACAAGACCTTTTGC-3'

(see SEQ ID NO:29)
DETECTION 1 = 5'-GACCCTGTAGGGTTACATT-3'

(see SEQ ID NO:106)
DETECTION 2 = 5'-TGACCTGTTGCTGTGGA-3'

EXAMPLE 13

Detection of the DNA sequence corresponding to the E7 genes of the human types 6 and 11 papillomavirus.

When the sequence to be detected is amplified DNA, the sequences used are as follows:

TRIGGER 1 = 5'-TACACTGCTGGACAACATGC-3' (see SEQ ID NO:34)

TRIGGER 2 = 5'-GTGCGCAGATGGGACACAC-3' (see SEQ ID NO:35)

The DNA, amplified or not, can be detected using the following system: (strand-detection):

CAPTURE 1 = 5'-AGACAGCTCAGAAGATGAGG-3' (see SEQ ID NO:36)

CAPTURE 2 = 5'-CAGCAACGT(T/C)CGACTGGTTG-3' (see SEQ ID NOS:37 and 111)

DETECTION 1 = 5'-GACCCTGTAGGGTTACATT-3' (see SEQ ID NO:29)

DETECTION 2 = 5'-TGACCTGTTGCTGTGGA-3' (see SEQ ID NO:106)

EXAMPLE 14

Detection of the DNA sequence corresponding to gene E7 of the human type 16 papillomavirus.

When the sequence to be detected is amplified DNA, the sequences used are as follows:

TRIGGER 1 = 5'-CCCAGCTGTAATCATGCATGGAGA-3' (see SEQ ID NO:38)

TRIGGER 2 = 5'-GTGTGCCCATTAACAGGTCTTCCA-3' (see SEQ ID NO:39)

The DNA, amplified or unamplified, can be detected using the following system (strand-detection):

CAPTURE 1 = 5'-TATATGTTAGATTTGCAACC-3' (see SEQ ID NO:40)

CAPTURE 2 = 5'-GACAACTGATCTCTAC-3' (see SEQ ID NO:41)

DETECTION 1 = 5'-CCGGACAGAGCCCATTAC-3' (see SEQ ID NO:42)

DETECTION 2 = 5'-CTCTACGCTTCGGTTGTGC-3' (see SEQ ID NO:43)

EXAMPLE 15

Detection of the DNA sequence corresponding to gene E7 of the human type 18 papillomavirus.

When the sequence to be detected is amplified DNA, the sequences used are the following ones:

TRIGGER 1 = 5'-CGACAGGAACGACTCCAACG-3' (see SEQ ID NO:44)

TRIGGER 2 = 5'-GCTGGTAAATGTTGATGATTAACT-3' (see SEQ ID NO:45)

The DNA, amplified or unamplified, may be detected using the following system (strand-detection):

CAPTURE 1 = 5'-TCAGAGGAAGAAAACGATGA-3' (see SEQ ID NO:46)

CAPTURE 2 = 5'-ATGTCACGAGCAATTAAGCG-3' (see SEQ ID NO:47)

DETECTION 1 = 5'-GTATTGCATTTAGAGCCCCA-3' (see SEQ ID NO:48)

DETECTION 2 = 5'-TAAGGCAACATTGCAAGACA-3' (see SEQ ID NO:49)

The DNA to be detected is denatured using the aforementioned protocol.

FIG. 2 represents the results obtained, the quantity of DNA being represented on the abscissa and the optical density, on the ordinate (FIG. 2 reveals that only HPV 18 is detected, while HPV 16 is not).

Sensitivity is approximately 1 ng of DNA.

EXAMPLE 16

System for detecting the human types 6, 11, 16, and 18 papillomaviruses.

The example describes the detection of each type after non-specific amplification, by means of chain reaction using a polymerase.

This reaction is carried out using a mixture of all of the oligonucleotides described in Examples 11, 12, 13, 14, and 15.

Each oligonucleotide is used in a concentration of 0.3 µM.

Capture is effected using all of the capture oligonucleotides described in Examples 11, 12, 13, 14, and 15 (passive adsorption, protocol described in Example 5).

Detection is performed specifically by using one of the peroxidase-marked oligonucleotide pairs described in Examples 11, 12, 13, 14, and 15.

The results and specificities obtained are as follows, excluding the case in which detection is performed on 1/100th of the amplification product (Table 18).

TABLE 18

| AMPLIFIED DNA | DETECTION SYSTEM | | |
| --- | --- | --- | --- |
| | HPV18 | HPV16 | HPV6/11 |
| HPV6 | 0.001 | 0.004 | 1.100 |
| HPV16 | 0.002 | 0.840 | 0.008 |
| HPV18 | 0.600 | 0.028 | 0.002 |
| HPV6 + 16 | 0.001 | 0.845 | 0.480 |
| HPV6 + 16 + 18 | 0.540 | 0.821 | 0.320 |
| HPV6 + 18 | 0.580 | 0.020 | 0.687 |
| HPV16 + 18 | 0.516 | 0.740 | 0.007 |
| Non-specific HPV2 | 0.001 | 0.018 | 0.002 |
| Water: non-specific control | 0.001 | 0.014 | 0.001 |

EXAMPLE 17

Detection of the DNA sequence corresponding to the gene of the principal protein of the external membrane (MOMP) of Chlamydia trachomatis. When the sequence to be detected is amplified DNA, the sequences used are as follows:

AMPLIFICATION TRIGGER 1 = 5'-CACCATAGTAACCCATACGC-3' (see SEQ ID NO:50)

AMPLIFICATION TRIGGER 2 = 5'-GCCGCTTTGAGTTCTGCTTCC-3' (see SEQ ID NO:51)

The DNA, amplified or not, may be detected using the following system (strand-detection):

CAPTURE 1 = 5'-GCCGCTTTGAGTTCTGCTTCC-3' (see SEQ ID NO:51)

CAPTURE 2 = 5'-CTTGCAAGCTCTGCCTGTGG-3' (see SEQ ID NO:53)

DETECTION 1 = 5'-AATCCTGGCTGAACCAAGCCT-3' (see SEQ ID NO:54)

DETECTION 2 = 5'-AAGGTTTCGGCGGAGATCCT-3' (see SEQ ID NO:55)

EXAMPLE 18

Detection of the DNA sequence corresponding to the gag region of the HIV 1 retrovirus.

When the sequence to be detected is amplified DNA, the sequences used are as follows:

TRIGGER 1 = 5'-GGACATCAAGCAGCCATGC-3' (see SEQ ID NO:56)

TRIGGER 2 = 5'-CTAGTAGTTCCTGCTATGTC-3' (see SEQ ID NO:57)

The DNA, amplified or unamplified, may be detected using the following system:

CAPTURE 1 = 5'-AATGTTAAAAGAGAC-3' (see SEQ ID NO:58)

DETECTION 1 = 5'-GAAGCTGCAGAATGGGA-3' (see SEQ ID NO:59)

EXAMPLE 19

Detection of the DNA sequence corresponding to the gag region of the HIV 2 retrovirus.

When the sequence to be detected is amplified DNA, the sequences used are as follows:

TRIGGER 1 = 5'-GACCATCAAGCAGCCATGC-3' (see SEQ ID NO:108)

TRIGGER 2 = 5'-CTTGTTGTCCCTGCTATGTC-3' (see SEQ ID NO:106)

The DNA, amplified or unamplified, can be detected using the following system:

CAPTURE 1 = 5'-CTTACCAGCGGGGCAGC-3' (see SEQ ID NO:61)

DETECTION 1 = 5'-GAAGCTGCAGAATGGGA-3' (see SEQ ID NOS:109)

EXAMPLE 20

Detection of the DNA sequence corresponding to the env region of the HIV 1 retrovirus.

When the sequence to be detected is amplified DNA, the sequences used are as follows:

TRIGGER 1 = 5'-CAGGAAGCACTATGGGCGC-3' (see SEQ ID NO:62)

TRIGGER 2 = 5'-GCTGCTTGATGCCCCAGAC-3' (see SEQ ID NO:63)

The DNA, amplified or unamplified, can be detected using the following system:

CAPTURE 1 = 5'-TGTCTGGTATAGTGCA-3' (see SEQ ID NO:64)

DETECTION 1 = 5'-AACAATTTGCTGAGGGCTAT-3' (see SEQ ID NO:65)

EXAMPLE 21

Detection of the DNA sequence corresponding to the env region of the HIV 2 retrovirus.

When the sequence to be detected is amplified DNA, the sequences used are as follows:

TRIGGER 1 = 5'-CAGGCAGTTCTGCAATGGG-3' (see SEQ ID NO:66)

TRIGGER 2 = 5'-GGTTTTTCGTTCCCCAGACG-3' (see SEQ ID NO:67)

The DNA, amplified or unamplified, can be detected using the following system:

CAPTURE 1 = 5'-GCAACAGCAACAGCTGTTGGA-3' (see SEQ ID NO:68)

DETECTION 1 = 5'-GGTCAAGAGACAACAAGAA-3' (see SEQ ID NO:69)

EXAMPLE 22

Detection of the DNA sequence corresponding to the pol region of the HIV 1 retrovirus.

When the sequence to be detected is amplified DNA, the sequences used are as follows:

TRIGGER 1 = 5'-ATTAGCAGGAAGATGGCCAG-3' (see SEQ ID NO:70)

TRIGGER 2 = 5'-CTGCCATTTGTACTGCTGGTC-3' (see SEQ ID NO:71)

The DNA, amplified or unamplified, can be detected using the following system:

CAPTURE 1 = 5'-GACAATGGCAGCAATTTCACC-3' (see SEQ ID NO:72)

DETECTION 1 = 5'-GCCTGTTGGTGGGC-3' (see SEQ ID NO:73)

EXAMPLE 23

Detection of the DNA sequence corresponding to the gene in the β glucuronidase region of *E. coli*.

When the sequence to be detected is amplified DNA, the sequences used are as follows:

TRIGGER 1 = 5'-CAATACGCTCGAACGACGT-3' (see SEQ ID NO:74)

TRIGGER 2 = 5'-CACGGGTTGGGGTTTCTAC-3' (see SEQ ID NO:75)

The DNA, amplified or unamplified, can be detected using the following system (strand-detection):

CAPTURE 1 = 5'-TGGCTTCTGTCAACGCTGTT-3' (see SEQ ID NO:76)

CAPTURE 2 = 5'-ATGCGATCTATATCACGCTG-3' (see SEQ ID NO:77)

DETECTION 1 = 5'-GATCGCGGTGTCAGTTCTTT-3' (see SEQ ID NOS:78)

-continued

DETECTION 2 = 5'-TTCCATGGGTTTCTCACAGA-3'   (see SEQ ID NOS:79)

EXAMPLE 24

Detection of the DNA sequence corresponding to the gene in the human β globin.

When the sequence to be detected is amplified DNA, the sequences used are as follows:

TRIGGER 1 = 5'-GACTCAGAATAATCCAGCCT-3' (see SEQ ID NO:80)

TRIGGER 2 = 5'-TGTTTACGCAGTCTGCCTAG-3' (see SEQ ID NO:81)

The DNA, amplified or unamplified, can be detected using the following system (strand-detection):

CAPTURE 1 = 5'-TGTTTACGCAGTCTGCCTAG-3'   (see SEQ ID NO:81)

CAPTURE 2 = 5'-CACATATTGACCAAATCAGG-3'   (see SEQ ID NO:83)

DETECTION 1 = 5'-GTATCATGCCTCTTTGCACC-3'   (see SEQ ID NOS:84)

DETECTION 2 = 5'-TTTCTGGGTTAAGGCAATAGC-3'   (see SEQ ID NO:85)

EXAMPLE 25

Detection of the DNA sequence corresponding to the ras oncogene.

When the sequence to be detected is amplified DNA, the sequences used are as follows:

TRIGGER 1 = 5'-TGTTATGATGGTGAAACCTG-3'   (see SEQ ID NO:86)

TRIGGER 2 = 5'-CTGTAGAGGTTAATATCCGCAAA-3'   (see SEQ ID NO:87)

The DNA, amplified or unamplified, can be detected using the following system (strand-detection):

CAPTURE 1 = 5'-CAGTGCCATGAGAGACCAAT-3'   (see SEQ ID NO:88)

CAPTURE 2 = 5'-CGACGCAGCCATGGTCGATGC-3'   (see SEQ ID NO:89)

DETECTION 1 = 5'-TTCCTCTGTGTATTTGCCAT-3'   (see SEQ ID NOS:90)

DETECTION 2 = 5'-ACATGAGGACAGGCGAAGGC-3'   (see SEQ ID NOS:105)

EXAMPLE 26

Use of peroxidase-marked alpha-oligonucleotide for detection.

Protocol as in Example 5.

Target: (see SEQ ID NOS:91)

The detection probe used is the alpha oligonucleotide 5'-ACCCCGAGATTTAGGTTATGT-3' (see SEQ ID NO:93) grafted to the horseradish peroxidase as described in Example 3. The detection limit is 5 pg of the target, or $5.10^{-17}$ moles (Table 19).

TABLE 19

| | target (pg) | | | | | |
|---|---|---|---|---|---|---|
| | 5000 | 500 | 50 | 5 | 0.5 | 0 |
| DO value | >2.5 | 0.622 | 0.073 | 0.025 | 0.008 | 0.007 |

EXAMPLE 27

Alkaline phosphatase as a detection enzyme for colorimetry.

Protocol identical to that in Example 5.

The detection probe 5'-TAAGGCAACATTGCAAGACA-3' (see SEQ ID NO:49) is coupled to the alkaline phosphatase, as described in Example 4.

100 μl of the PNPP substrate (Sigma 104-0) in a concentration of 2 mg/ml (in a buffer containing 1.29M diethanolamine, 0.58 mM MgSO$_4$, 0.38 mM naN$_3$; 0.12N HCl, pH=9.8) are added per well. After a 20-minute reaction time, enzymatic activity is blocked by means of 100 μl of NaOH 1N, and the reading is made on an Axia Microreader (BioMérieux) at 402 nm.

CAPTURE(see SEQ ID NO:46)=5'-TCAGAGGAAGAAAACGATGA-3'

Target: pBR 322 plasmid containing 20 μg/ml of the type 18 PVH gene.

TABLE 20

| | dilution of target | | | | | |
|---|---|---|---|---|---|---|
| | 100 | 500 | 1000 | 2000 | 5000 | blank |
| DO value | 0.505 | 0.086 | 0.054 | 0.029 | 0.008 | 0.008 |

The detection limit is 1/2000th of the target (Table 20), i.e., approximately 500 pg, or $1.8 \times 10^{-16}$ mole.

EXAMPLE 28

Alkaline phosphatase as a detection enzyme under fluorescence.

The protocol is the same as that used in Example 27, but, as substrate, 100 μl of methyl-4 umbelliferylphosphate (MUP, Boehringer ref. 405663) in a buffer containing 100 mM glycino-NaOH, 1 mM MgCl$_2$, 0.1 mM ZnCl$_2$, 0.5 g/l NaN$_3$m pH=10.3, in a concentration of 80 μg/ml, are added.

The reaction is blocked after 20 minutes with 100 μl of a mixture of 0.5M KH$_2$PO, pH 10.4 and 10 mM EDTA. Reading is performed on a fluorometer (excitation 340 nm, emission 460 nm) (Table 21).

5'-TCATCGTTTTCTTCCTCTGAGTCGCTTAATTGCTCGTGACATAGAAGGTCAACCG
GAATTTCATTTTGGGGCTCTAAATGCAATACAATGTCTTGCAATGTTGCCTTA-3'

CAPTURE = 5'-TCAGAGGAAGAAAACGATGA-3'   (see SEQ ID NOS:46)

TABLE 21

| | dilution of target | | | | | |
|---|---|---|---|---|---|---|
| | 100 | 500 | 1000 | 2000 | 5000 | blank |
| unities of fluorescence | 643 | 167 | 94 | 82 | 66 | 47 |

EXAMPLE 29

Detection of HIV 1 virus.
a) NEF Region
The following sequences are used for amplification:

TRIGGER 1: 5'-CATTGGTCTTAAAGGTACCTG-3'  (see SEQ ID NO:95)

TRIGGER 2: 5'-AAGATGGGTGGCAATTGGTC-3'  (see SEQ ID NO:96)

The capture and detection probes are as follows:

(see SEQ ID NO:97)
CAPTURE: 5'-GAGGAGGTTGGTTTTCCAGTCA-3'

(see SEQ ID NOS:110)
DETECTION: 5'-GGATGGCCTTCTTTAAGGGAAAGAATG-3' b) VFE Region

The following sequences are used for amplification:

(see SEQ ID NO:98)
TRIGGER 1: 5'-TGGAACAAGCCCCAGTAGACC-3'

(see SEQ ID NO:99)
TRIGGER 2: 5'-TGCTATGTTGACACCCAATTCTG-3'

The capture and detection probes are as follows:

(see SEQ ID NO:100)
CAPTURE: 5'-TATGAAACTTATGGGGATAC-3'

(see SEQ ID NOS:3)
DETECTION: 5'-GAAGCTGTTAGACATTTTCCTAG-3' c) POL Region
The capture and detection probes are as follows:

(see SEQ ID NO:102)
CAPTURE: 5'-TGAACAAGTAGATAAATTAG-3'

(see SEQ ID NOS:103)
DETECTION: 5'-GGAATCAGTAAAGTACTATT-3'.

---

We claim:

1. Procedure for the detection of a single-stranded polynucleotide target sequence in a sample, comprising the steps consisting of:
 a) incubating the sample:
  i) with a capture probe adsorbed to a hydrophobic solid support, wherein said capture probe is an oligonucleotide having from 11 to 19 nucleotides and said capture probe is not derivatized with a moiety to facilitate adsorption, and
  ii) with a detection probe labelled with a non-radioactive marker, said capture probe and said detection probe being capable of hybridizing with two non-overlapping regions of said target sequence, b) washing said solid support in order to remove material not bound to said support by hybridization, and c) determining whether said marker is bound to said support, the presence of said marker indicating the presence of said single-stranded polynucleotide sequence in said sample.

2. Procedure for the detection of the presence or absence of a single base mutation in a single-stranded nucleotide target sequence, in a sample, comprising the steps of:

a) incubating said sample at a first temperature:
  i) with a capture probe adsorbed to a hydrophobic solid support, wherein said capture probe is an oligonucleotide having from 11 to 19 nucleotides and said capture probe is not derivatized with a moiety to facilitate adsorption, and
  ii) with a detection probe labelled with a non-radioactive marker,
    said capture probe and said detection probe being substantially complementary to two non-overlapping regions of said target sequence, and said single base mutation, if present, being in the region of said target sequence which is substantially complementary to the sequence of said capture probe, b) washing said solid support at a second temperature in order to remove material non-bound to said support by hybridization, and c) determining whether said marker is bound to said support,
  with the proviso that at least one of said first temperature and said second temperature is a temperature at which said capture probe will hybridize to only a completely complementary sequence in said target sequence, if present, and with the proviso that said capture probe is either
  i) completely complementary to said target sequence containing said single base mutation or
  ii) completely complementary to said target sequence not containing said single base mutation,
    whereby the absence of said marker in proviso i) or the presence of said marker in proviso ii) indicates the absence of said single base mutation in said target sequence, and
    whereby the presence of said marker in proviso i) or the absence of said marker in proviso ii) indicates the presence of said single base mutation in said target sequence.

3. The procedure according to claim 2 wherein at least one of said first temperature and said second temperature is in the range of 20° C. to 60° C.

4. The procedure according to claim 3 wherein at least one of said first temperature and said second temperature is in the range of 25° C. to 40° C.

5. The procedure according to claim 4 wherein at least one of said first temperature and said second temperature is 37° C.

6. The procedure according to claim 1 wherein said support is a tube, ball, particle, pipetting cone, or microtitration plate.

7. The procedure according to claim 2 wherein said support is a tube, ball, particle, pipetting cone, or microtitration plate.

8. The procedure according to claim 1 wherein said target sequence is a messenger RNA sequence corresponding to a gene encoding beta-lactamase of *E. coli* (Tem) and wherein said capture probe is at least one of SEQ ID NO:1 or SEQ ID NO:8.

9. The procedure according to claim 8 wherein said detection probe contains at least one of SEQ ID NO:17 or SEQ ID NO:18.

10. The procedure according to claim 1 wherein said target sequence is a DNA sequence containing a gene encoding beta-lactamase of *E. coli* and wherein said capture probe is at least one of SEQ ID NO:19 or SEQ ID NO:20.

11. The procedure according to claim 10 wherein said detection probe contains at least one of SEQ ID NO:21 or SEQ ID NO:22.

12. The procedure according to claim 1 wherein said target sequence is a DNA sequence corresponding to the E7 gene of the human type 6 papilloma virus and wherein said capture probe is at least one of SEQ ID NO:27 or SEQ ID NO:28.

13. The procedure according to claim 12 wherein said detection probe contains at least one of SEQ ID NO:29 or SEQ ID NO:106.

14. The procedure according to claim 1 wherein said target sequence is a DNA sequence corresponding to the E7 gene of the human type 11 papilloma virus and wherein said capture probe is at least one of SEQ ID NO:28 or SEQ ID NO:33.

15. The procedure according to claim 14 wherein said detection probe contains at least one of SEQ ID NO:29 or SEQ ID NO:106.

16. The procedure according to claim 1 wherein said target sequence is a DNA sequence corresponding to an E7 gene of the human type 16 papilloma virus and said capture probe is SEQ ID NO:41.

17. The procedure according to claim 16 wherein said detection probe contains at least one of SEQ ID NO:43 or SEQ ID NO:42.

18. The procedure according to claim 1 wherein said target sequence is a DNA sequence corresponding to the gag region of the HIV 1 retrovirus and said capture probe is SEQ ID NO:58.

19. The procedure according to claim 18 wherein said detection probe contains SEQ ID NO:59.

20. The procedure according to claim 1 wherein said target sequence corresponds to the gag region of the HIV 2 retrovirus and said capture probe is SEQ ID NO:61.

21. The procedure according to claim 20 wherein said detection probe contains SEQ ID NO:59.

22. The procedure according to claim 1 wherein said target sequence corresponds to the env region of the HIV 1 retrovirus and said capture probe is SEQ ID NO:64.

23. The procedure according to claim 22 wherein said detection probe contains SEQ ID NO:65.

* * * * *